(12) United States Patent
Patangay et al.

(10) Patent No.: US 7,678,058 B2
(45) Date of Patent: Mar. 16, 2010

(54) APNEA TYPE DETERMINING APPARATUS AND METHOD

(75) Inventors: Abhilash Patangay, Little Canada, MN (US); Yachuan Pu, Minneapolis, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 734 days.

(21) Appl. No.: 11/425,820

(22) Filed: Jun. 22, 2006

(65) Prior Publication Data

US 2008/0009755 A1    Jan. 10, 2008

(51) Int. Cl.
*A61B 5/08* (2006.01)
(52) U.S. Cl. ................. 600/484; 600/485; 600/486; 600/529
(58) Field of Classification Search ............... 600/484, 600/485, 506, 529
See application file for complete search history.

(56) References Cited

U.S. PATENT DOCUMENTS

| | | | |
|---|---|---|---|
| 4,129,125 A * | 12/1978 | Lester et al. ............... 600/484 |
| 4,648,407 A | 3/1987 | Sackner |
| 4,777,962 A | 10/1988 | Watson et al. |
| 5,146,918 A | 9/1992 | Kallok et al. |
| 5,174,287 A | 12/1992 | Kallok et al. |
| 5,215,082 A | 6/1993 | Kallok et al. |
| 5,275,159 A | 1/1994 | Griebel |
| 5,368,040 A | 11/1994 | Carney |
| 5,385,144 A * | 1/1995 | Yamanishi et al. ........ 600/330 |
| 5,458,137 A | 10/1995 | Axe et al. |
| 5,935,081 A | 8/1999 | Kadhiresan |
| 5,974,340 A | 10/1999 | Kadhiresan |
| 6,064,910 A | 5/2000 | Andersson et al. |
| 6,076,015 A | 6/2000 | Hartley et al. |
| 6,126,611 A | 10/2000 | Bourgeois et al. |
| 6,208,900 B1 | 3/2001 | Ecker et al. |
| 6,368,283 B1 | 4/2002 | Xu et al. |
| 6,527,729 B1 | 3/2003 | Turcott |
| 6,641,542 B2 | 11/2003 | Cho et al. |
| 6,856,829 B2 | 2/2005 | Ohsaki et al. |
| 6,865,419 B2 | 3/2005 | Mulligan et al. |

(Continued)

FOREIGN PATENT DOCUMENTS

EP    1488743 A2    12/2004

(Continued)

OTHER PUBLICATIONS

Brooks, D., et al., "Obstructive Sleep Apnea as a Cause of Systemic Hypertension", *J Clin Invest.*, 99(1), (Jan. 1, 1997), 106-9.

(Continued)

*Primary Examiner*—Robert L Nasser
*Assistant Examiner*—Michael D'Angelo
(74) *Attorney, Agent, or Firm*—Schwegman, Lundberg & Woessner, P.A.

(57) ABSTRACT

An apnea classification system provides for apnea monitoring and differentiation based on several sleep apnea related parameters for diagnostic and therapeutic purposes. Monitoring of such sleep apnea related parameters allows the apnea classification system to differentiate among the different types of apnea. This information may then be used to determine the best method of therapy, or adjust current therapy parameters to more effectively treat a subject.

30 Claims, 6 Drawing Sheets

U.S. PATENT DOCUMENTS

| | | | |
|---|---|---|---|
| 6,869,404 | B2 | 3/2005 | Schulhauser et al. |
| 6,887,207 | B2 | 5/2005 | Hettrick |
| 6,918,878 | B2 | 7/2005 | Brodnick |
| 7,225,021 | B1 * | 5/2007 | Park et al. ............ 607/18 |
| 7,510,531 | B2 | 3/2009 | Lee et al. |
| 2002/0029000 | A1 | 3/2002 | Ohsaki et al. |
| 2002/0185130 | A1 | 12/2002 | Wright et al. |
| 2004/0134496 | A1 | 7/2004 | Cho et al. |
| 2005/0217674 | A1 | 10/2005 | Burton et al. |
| 2005/0222502 | A1 | 10/2005 | Cooper |
| 2005/0261600 | A1 | 11/2005 | Aylsworth |
| 2007/0142727 | A1 * | 6/2007 | Zhang et al. ............ 600/486 |

FOREIGN PATENT DOCUMENTS

| | | |
|---|---|---|
| EP | 1551286 A2 | 7/2005 |

OTHER PUBLICATIONS

Chen, L., et al., "Hemodynamic effects of periodic obstructive apneas in sedated pigs with congestive heart failure", *J Appl Physiol.*, 88(3), (Mar. 2000), 1051-60.

Chen, L., et al., "Systemic and myocardial hemodynamics during periodic obstructive apneas in sedated pigs", *J Appl Physiol.*, 84(4), (Apr. 1998), 1289-98.

Parker, J. D., et al., "Acute and chronic effects of airway obstruction on canine left ventricular performance", *Am J Respir Crit Care Med.*, 160(6), (Dec. 1999), 1888-96.

Schneider, H., et al., "Effects of arousal and sleep state on systemic and pulmonary hemodynamics in obstructive apnea", *Journal of Applied Physiology*, 88(3), (Mar. 2000), 1084-1092.

Schneider, H., et al., "Systemic and pulmonary hemodynamic responses to normal and obstructed breathing during sleep", *J Appl Physiol.*, 83(5), (Nov., 1997), 1671-80.

Tilkian, A. G., et al., "Hemodynamics in sleep-induced apnea. Studies during wakefulness and sleep.", *Ann Intern Med.*, 85(6), (Dec. 1976), 714-9.

Tkacova, R., et al., "Effects of continuous positive airway pressure on obstructive sleep apnea and left ventricular afterload in patients with heart failure", *Circulation.*, 98(21), (Nov. 24, 1998), 2269-75.

Virolainen, J., et al., "Effect of negative intrathoracic pressure on left ventricular pressure dynamics and relaxation", *J Appl Physiol.*, 79(2), (Aug. 1995), 455-60.

* cited by examiner

APNEA TYPE DETERMINING APPARATUS AND METHOD

TECHNICAL FIELD

This patent document pertains generally to implantable medical devices, and more particularly, but not by way of limitation, to a method and apparatus for determining the type of sleep apnea in a patient.

BACKGROUND

Sleep apnea involves a brief cessation of breathing during sleep. There exist two types of sleep apnea: central sleep apnea ("CSA"), which is associated with the failure of the body to automatically initiate and control a respiratory cycle at the proper time; and obstructive sleep apnea ("OSA"), which is associated with a blockage of the airway.

The most common type of sleep apnea is central sleep apnea. Central sleep apnea typically causes cessation of substantially all respiratory effort during sleep. This condition may be developed after a heart attack, and is usually a contributing factor to heart failure and other cardiopulmonary disorders.

The other type of sleep apnea is obstructive sleep apnea. Obstructive sleep apnea is generally characterized by repetitive pauses in breathing during sleep due to upper airway obstruction or collapse and is commonly found in overweight people who snore or have oversized necks. When awake, muscle tone keeps the throat open. When asleep, the airway of the neck narrows and closes. The person struggles to breathe against the collapsed throat as if choking. As the patient wakes up, the muscles of the throat open the airway. Many patients with congestive heart failure ("CHF") suffer from obstructive sleep apnea.

Heart condition is typically worsened by excessive stress during apnea. Thus, the detection of sleep apnea is important.

Sleep apnea, once diagnosed in a patient, may be treated through several methods, including continuous positive airway pressure ("CPAP"), and electrical stimulation of the heart, diaphragm, or upper airway muscles.

Presently, sleep apnea detection is accomplished by several methods, including the detection of respiration, such as by monitoring the transthoracic impedance and other techniques.

SUMMARY

When detecting sleep apnea through respiration, it is difficult to differentiate between the different types of sleep apnea, mainly obstructed sleep apnea and central sleep apnea. This document describes an improved method and apparatus for detecting and determining the type of sleep apnea in a patient.

An apnea classification system provides for apnea monitoring and differentiation based on several sleep apnea related parameters for diagnostic and therapeutic purposes. Monitoring of such sleep apnea related parameters allows the apnea classification system to differentiate among the different types of apnea. This information may then be used to determine the best method of therapy, or adjust current therapy parameters to more effectively treat a subject.

In one example, a system includes multiple apnea detectors and an apnea classification module. A first apnea detector is respiration-based and is indicative of a general apnea event, or a cessation of breathing for a period of time. A second apnea detector is non-respiration-based and is indicative of a specific type of apnea. The apnea classification module receives data from both sensors and differentiates between the different types of apnea, namely obstructive sleep apnea and central sleep apnea. Therapy can then be implemented based upon the type of apnea determined.

The respiration-based apnea detector may be implemented in several ways. In one example, the respiration-based apnea detector comprises of at least one of a respiration sensor, an impedance sensor, a pressure sensor, an accelerometer, a heart sound sensor, an acoustic sensor, a position sensor, or a thermister.

The non-respiration-based apnea detector may be implemented in several ways. In one example, the non-respiration-based apnea detector comprises of at least one of a pressure sensor and a heart sound sensor, in which the pressure sensor comprises of at least one of a pulmonary artery pressure sensor and a left ventricle pressure sensor, and the heart sound sensor comprises of at least one of an acoustic sensor, an accelerometer, a position sensor, or an activity sensor.

In another example, a method includes sensing a respiration signal, detecting at least one of a blood pressure signal and a heart sound signal, detecting an apnea event from at least one of a respiration signal, a blood pressure signal, and a heart sound signal, and distinguishing between obstructive sleep apnea and central sleep apnea using information from the respiration signal and information from at least one of the blood pressure signal and the heart sound signal. Therapy can then be implemented based on the type of apnea determined.

A respiration signal may be sensed in several ways. In one example, sensing the respiration signal comprises of at least one of sensing a thoracic impedance, extracting respiration information from a blood pressure signal, extracting respiration information from an acceleration, extracting respiration information from heart sounds, extracting respiration information from an acoustic sensor, extracting respiration information from a temperature.

A blood pressure signal may be detected in several ways. In one example, detecting a blood pressure signal comprises at least one of sensing pulmonary artery blood pressure and sensing left ventricle blood pressure.

This summary is intended to provide an overview of the subject matter of the present patent application. It is not intended to provide an exclusive or exhaustive explanation of the invention. The detailed description is included to provide further information about the subject matter of the present patent application.

DETAILED DESCRIPTION

The following detailed description includes references to the accompanying drawings, which form a part of the detailed description. The drawings show, by way of illustration, specific embodiments in which the invention may be practiced. These embodiments, which are also referred to herein as "examples," are described in enough detail to enable those skilled in the art to practice the invention. The embodiments may be combined, other embodiments may be utilized, or structural, logical and electrical changes may be made without departing from the scope of the present invention. The following detailed description is, therefore, not to be taken in a limiting sense, and the scope of the present invention is defined by the appended claims and their equivalents.

In this document, the terms "a" or "an" are used, as is common in patent documents, to include one or more than one. In this document, the term "or" is used to refer to a nonexclusive or, unless otherwise indicated. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

As a person is experiencing obstructive sleep apnea, certain indicators are present that are absent during a central sleep apnea event. Certain other indicators are present during a central sleep apnea event that are absent during an obstructive sleep apnea event. Other indicators are present during both types of events. Thus, by collecting multiple indicators of sleep apnea and comparing their results, the type of sleep apnea can better be determined.

Figure 1:
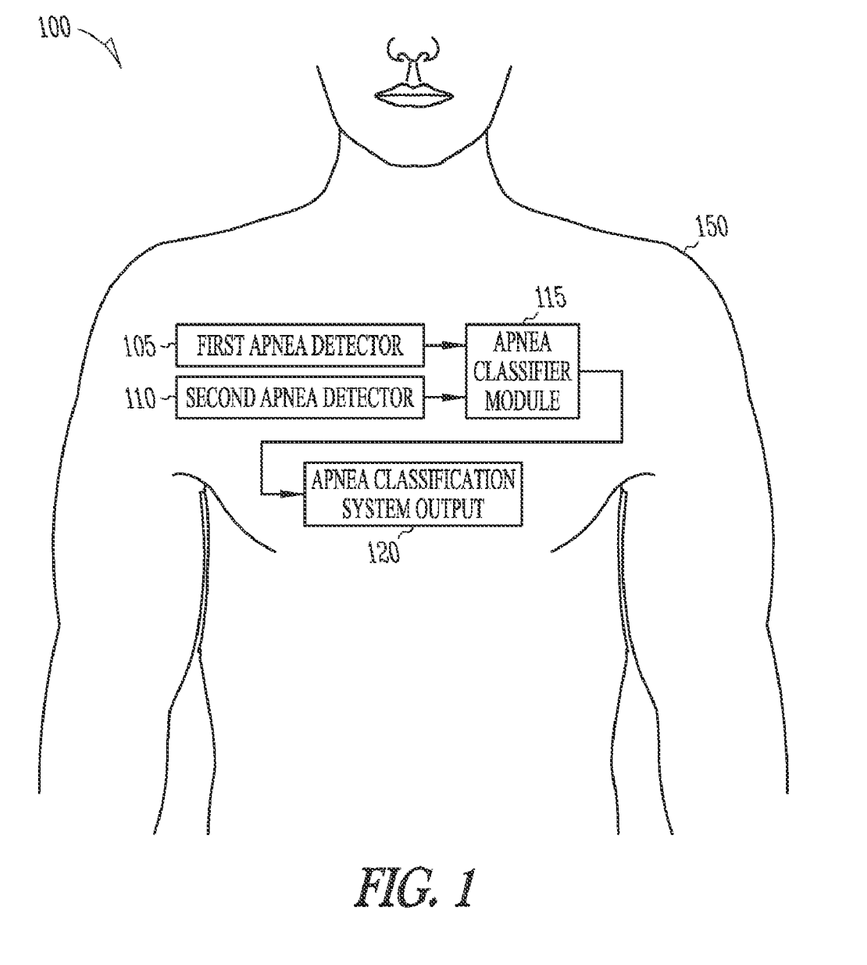
FIG. 1 is a schematic/block diagram illustrating generally the basic apparatus components according to one example.

FIG. 1 is a schematic/block diagram illustrating generally, by way of example, but not by way of limitation, one example of the basic apparatus components of an apnea classification system 100. System 100 includes, among other things, an apnea classifier module 115 for receiving data from a first implantable or external apnea detector 105 and a second implantable or external apnea detector 110.

First apnea detector 105 is respiration-based, and typically includes a respiration sensor. A respiration-based apnea detector senses, either directly or indirectly, whether the subject is breathing to detect apnea. The respiration-based apnea detector produces a sensor signal that includes cyclic variations indicative of inhaling and exhaling. For example, a thoracic impedance sensor includes cyclic variations as the subject inhales or exhales. In certain other examples, blood pressure and heart sound signals include components that are indicative of cyclic variations as the subject inhales or exhales. When so configured, a blood pressure sensor or a heart sound sensor may also be considered a respiration-based apnea detector.

Second apnea detector 110 is non-respiration-based, and typically includes at least one of a blood pressure sensor or a heart sound sensor. A non-respiration-based apnea detector senses, either directly or indirectly, a parameter indicative of apnea other than whether the subject is breathing. For example, certain other components of blood pressure and heart sound signals do not include the cyclic variations resulting from inhaling and exhaling. However, such other components of blood pressure and heart sound signals may have other information relevant to whether apnea is present or whether a type of apnea is present, as discussed below. As an illustrative first example of such a non-respiration indicator of apnea, there may be a change in left ventricle end diastolic pressure (LVEDP) during inspiratory efforts against a closed airway. Because the airway is closed, there is generally no cyclic variation in the pressure signal arising from inhaling or exhaling. However, during such an apnea episode, the LVEDP tends to gradually change over a time period that would correspond to several respiratory cycles, if such respiratory cycles were present. See, e.g., from 210 to 215 in FIG. 2, discussed below. Although such a change is affected by respiration, since it does not manifest cyclic information corresponding to inhaling and exhaling cycles, it is not considered to be a respiration sensor within the meaning of this document. As an illustrative second example, there may be gradual rise in S1 heart sound amplitude during obstructed breathing. See, e.g., from 325 to 330 in FIG. 3, as discussed below. Although heart sound information can be used to extract cyclic variations resulting from inhaling and exhaling, the gradual rise in S1 heart sound amplitude during obstructed breathing does not provide such cyclic variations from inhaling and exhaling. Thus, this component of the heart sound signal is not considered to be a respiration sensor within the meaning of this document.

Apnea classifier module 115 receives information from first apnea detector 105 and second apnea detector 110, and provides a resulting apnea classification at apnea classification system output 120.

In one example, apnea classifier module 115 receives data from first apnea detector 105 and second apnea detector 110. Using information from each, the apnea classifier module determines the type of apnea present within the subject, and outputs the resulting apnea classification at apnea classification system output 120.

Figure 1A:
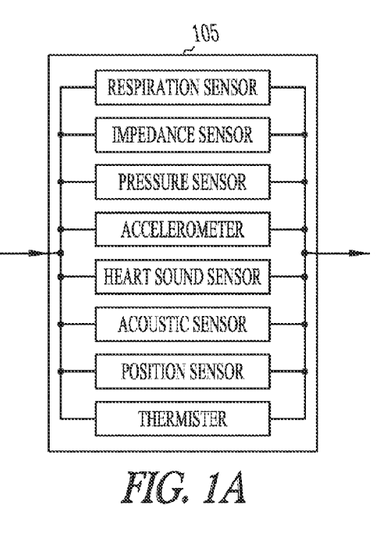
FIG. 1A is a schematic/block diagram illustrating apnea detector components according to one example.

FIG. 1A is a schematic/block diagram illustrating generally, by way of example, but not by way of limitation, one example of implementing first apnea detector 105 of apnea classification system 100. First apnea detector 105 typically includes a respiration sensor, such as a thoracic or intracardiac impedance-based respiration sensor, a blood pressure based respiration sensor, and accelerometer based respiration sensor, a heart sound sensor for respiration sensing, a position sensor for determining respiration, or a thermister for sensing respiration.

Figure 2:
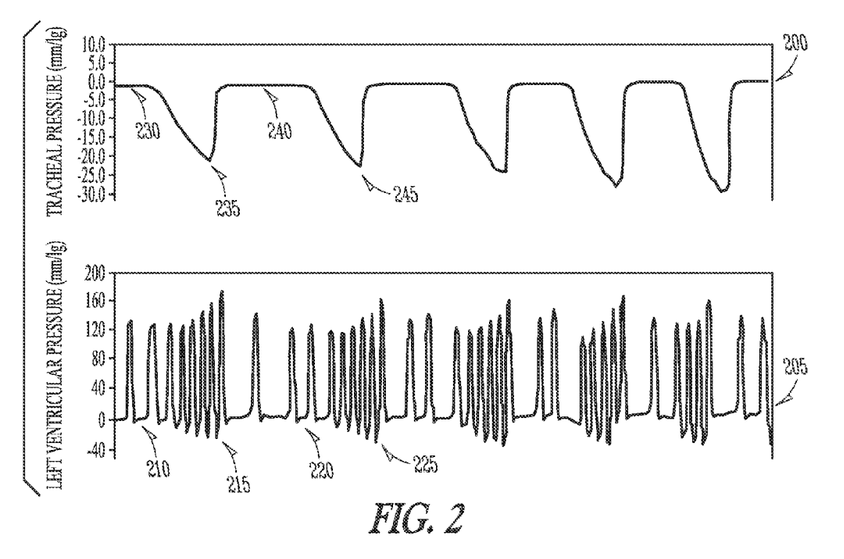
FIG. 2 is a graphical illustration of tracheal pressure and absolute left ventricular pressure during a series of inspiratory efforts against a closed airway.

In one example, respiration is detected by a respiration sensor placed over the mouth, the nasal openings, or both. In another example, respiration is detected by a transthoracic impedance sensor, as illustrated in FIG. 2. In another example, respiration is detected by a pressure sensor monitoring pressure changes in the body indicative of respiration. In another example, respiration is detected by an accelerometer, placed in a manner capable of detecting respiration. In another example, respiration is detected by a heart sound sensor, implanted in the subject 150 or located externally from the subject 150, indicative of respiration. In another example, respiration is detected by an acoustic sensor monitoring respiratory sounds indicative of respiration. In another example, respiration is detected by a position sensor, placed to monitor movement indicative of respiration. In another example, respiration is detected by a thermister located as to monitor temperature changes indicative of respiration, such as outside the nasal openings.

Figure 1B:
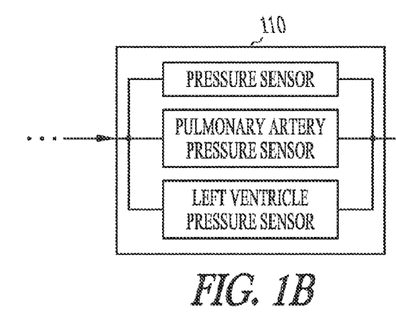
FIG. 1B is a schematic/block diagram illustrating apnea detector components according to one example.

FIG. 1B is a flow chart illustrating generally, by way of example, but not by way of limitation, one example of implementing second apnea detector 110 of apnea classification system 100, such as by using a pressure sensor.

In one example, second apnea detector 110 comprises a pulmonary artery pressure sensor. Recurrent upper airway obstructions, such as those present in obstructive sleep apnea, typically disrupt the stable systemic and pulmonary arterial pressures during sleep with normal breathing. Therefore, by extracting pulmonary artery pressure measurements from a pulmonary artery pressure sensor and conditioning the signal, obstructive sleep apnea can be detected.

In one example, a pulmonary artery pressure signal is extracted from a pulmonary artery pressure sensor. The signal is then filtered, e.g., by computing a moving average over a number of cardiac cycles. Other means, such as zero-cross threshold detection, differentiation, and peak detection, can then be used to analyze the signal and detect signature variations in the pulmonary artery pressure. A period of elevated average pulmonary artery pressure over multiple cycles may be indicative of obstructive sleep apnea.

In another example, second apnea detector 110 comprises a left ventricle pressure sensor. Obstructed inspirations, such as are present in obstructive sleep apnea, typically cause transient, but substantial, increases in left ventricle afterload. Left ventricle afterload typically denotes the pressure the left ventricle has to generate in order to eject blood. FIG. 2 shows that left ventricle end diastolic pressure (LVEDP) drops from 3 mmHg before the obstruction, to −15 mmHg during the obstruction. Therefore, by extracting left ventricle pressure measurements from a left ventricle pressure sensor and conditioning the signal to obtain LVEDP, obstructive sleep apnea can be detected.

Figure 1C:
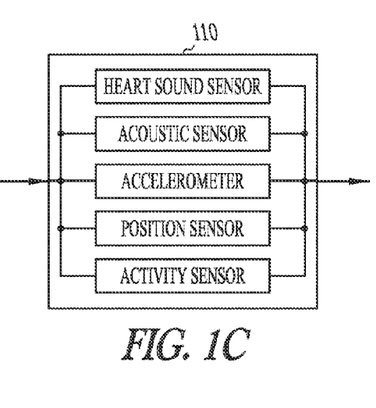
FIG. 1C is a schematic/block diagram illustrating apnea detector components according to one example.

FIG. 1C is a flow chart illustrating generally, by way of example, but not by way of limitation, one example of implementing second apnea detector 110 of apnea classification system 100, such as by using a heart sound sensor.

Figure 3:
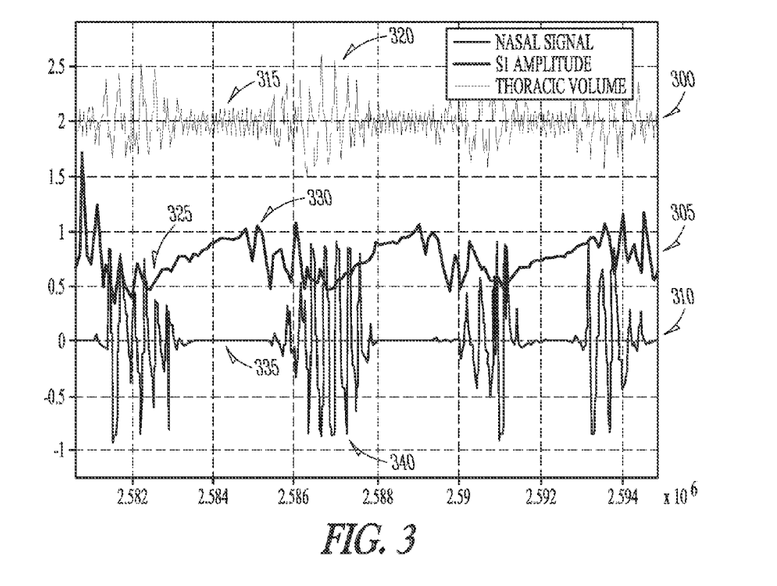
FIG. 3 is a graphical illustration of thoracic volume, S1 amplitude, and nasal signal during a series of inspiratory efforts against a closed airway.

In one example, second apnea detector 110 comprises a heart sound sensor. The normal first heart sound, S1, typically arises as the sound from the mitral valve closure followed by the tricuspid valve closure. Increased ventricular pressure typically increases the intensity of S1, as illustrated in FIG. 3. Lung volume typically changes during respiration. This change causes the volume of blood entering the heart to change. Thus, due to this normal "preload" change, the S1 intensity changes with the increase in blood entering the heart. Because obstructed inspirations cause transient, but substantial, increases in left ventricle afterload, S1 intensity and modulation can be used to detect obstructive sleep apnea.

FIG. 2 is a graphical illustration of a tracheal pressure signal 200 and a left ventricular pressure signal 205 during a series of inspiratory efforts against a closed airway. Inspiratory efforts in tracheal pressure signal 200 are easily identified as the periods in which the tracheal pressure signal 200 goes from positive, at 230, to negative, at 235. A second inspiratory effort is visible as the tracheal pressure signal 200 goes from positive, at 240, to negative, at 245. The pressure spikes in the left ventricle pressure signal 205 are typically indicative of heart muscle contractions. Inspiratory efforts in the left ventricle pressure signal 205 are identified as the periods in which the diastolic baseline of the left ventricle pressure signal 205 goes from positive, 3 mmHg at 210, to negative, −15 mmHg at 215. A second inspiratory efforts is visible as the diastolic baseline of the left ventricle pressure signal 205 goes from positive, 3 mmHg at 220, to negative, −15 mmHg at 225. Thus, the left ventricle pressure signal 205 may be indicative of obstructed sleep apnea.

FIG. 3 is a graphical illustration of a thoracic volume signal 300, S1 amplitude signal 305, and a nasal signal 310 during a series of inspiratory efforts against a closed airway. Each sinusoidal fluctuation in the nasal signal 310 is typically indicative of an individual respiration. Periods of closed airway typically are identified as those where nasal signal 310 is zero, e.g., 335. Periods of breathing typically are identified where nasal signal 310 is not zero, e.g., 340. During zero nasal flow, e.g., 335, S1 amplitude increases, e.g., from 325 to 330. This increase typically occurs over a time period that would correspond to several respiratory cycles, if such breathing were occurring. Thus, such an increase in the S1 amplitude signal 305 may be indicative of obstructed sleep apnea.

Periods of breathing may be identified in the thoracic volume signal 300, e.g., 320. However, periods of closed airway, typically identified as periods of zero nasal flow, e.g., 335, may be non-zero in the thoracic volume signal 300, e.g., 315. This non-zero reading in the thoracic volume signal 300 is typically due to changes in thoracic volume as the subject attempts to breathe. Thus, in some instances, a heart sound sensor will detect obstructive sleep apnea where some respiration sensors, e.g., a thoracic volume sensor, do not.

Figure 4A:
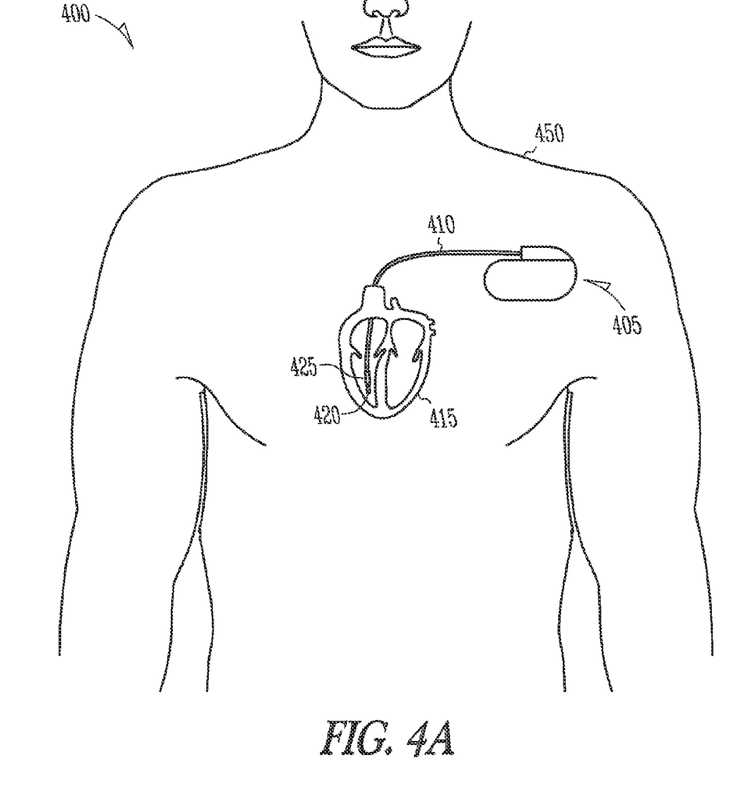
FIG. 4A is a schematic/block diagram illustrating impedance sensor components according to one example.
Figure 4B:
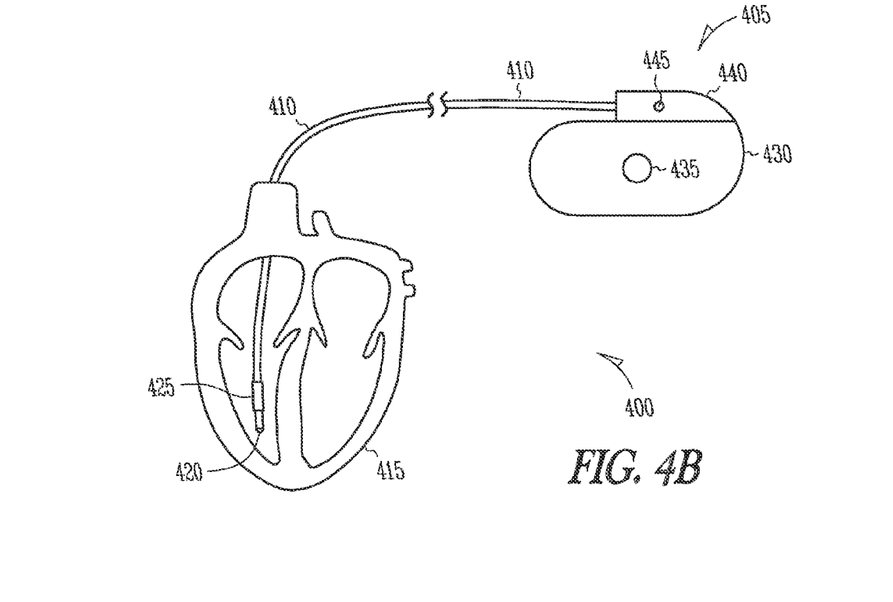
FIG. 4B is a schematic/block diagram illustrating impedance sensor components according to one example.

FIG. 4A and FIG. 4B are schematic/block diagrams illustrating generally, by way of example, but not by way of limitation, one example of implementing first apnea detector 105 by using an impedance sensor system 400. In this example, system 400 includes, among other things, a cardiac rhythm management device 405 and leadwire ("lead") 410 with tip electrode 420 and ring electrode 425 for communicating signals between device 405 and a portion of the subject 450, such as heart 415. Examples of device 405 include bradycardia and antitachycardia pacemakers, cardioverters, defibrillators, combination pacemaker/defibrillators, drug delivery devices, and any other cardiac rhythm management apparatus capable of providing therapy to heart 415.

In one example, system 400 is a transthoracic impedance sensor, such as described in Hartley et al. U.S. Pat. No. 6,076, 015 entitled "RATE ADAPTIVE CARDIAC RHYTHM MANAGEMENT DEVICE USING TRANSTHROACIC IMPEDANCE," assigned to Cardiac Pacemakers, Inc., the disclosure of which is incorporated herein by reference. Other impedance or other detectors may also be used for sensing respiration.

In one example, a first conductor of multiconductor lead 410 electronically couples a first electrode, such as tip electrode 420 (e.g., disposed at the apex of the right ventricle of heart 415), to device 405. A second conductor of multiconductor lead 410 independently electrically couples a second electrode, such as ring electrode 425, to device 405. In one example, device 405 includes a hermetically sealed housing 430, formed from a conductive metal, such as titanium. Housing 430 (also referred to as a "case" or "can") is substantially covered over its entire surface by a suitable insulator, such as silicone rubber, except for at a window that forms a third electrode, referred to as a "case" or "can" electrode 435. In one embodiment, a header 440 is mounted on housing 430 for receiving lead 410. Header 440 is formed of an insulative material, such as molded plastic. Header 440 also includes at least one receptacle, such as for receiving lead 410 and electrically coupling conductors of lead 410 to device 405. Header 440 can also include a fourth electrode, referred to as indifferent electrode 445.

In one example, an excitation signal, such as a strobed sequence of current pulses or other measurement stimuli, to heart 415 (e.g., between ring electrode 425 and tip electrode 420, or using any other electrode configuration suitable for such excitation). In response to the excitation signal, a response signal is sensed in the cardiac rhythm management device 405 (e.g., between tip electrode 420 and indifferent electrode 445, or any other suitable electrode configuration).

In one example, the response signal sensed by the cardiac rhythm management device 405 is a voltage that represents transthoracic (i.e., across a portion of the chest or thorax) impedance, which includes respiration information.

Figure 5:
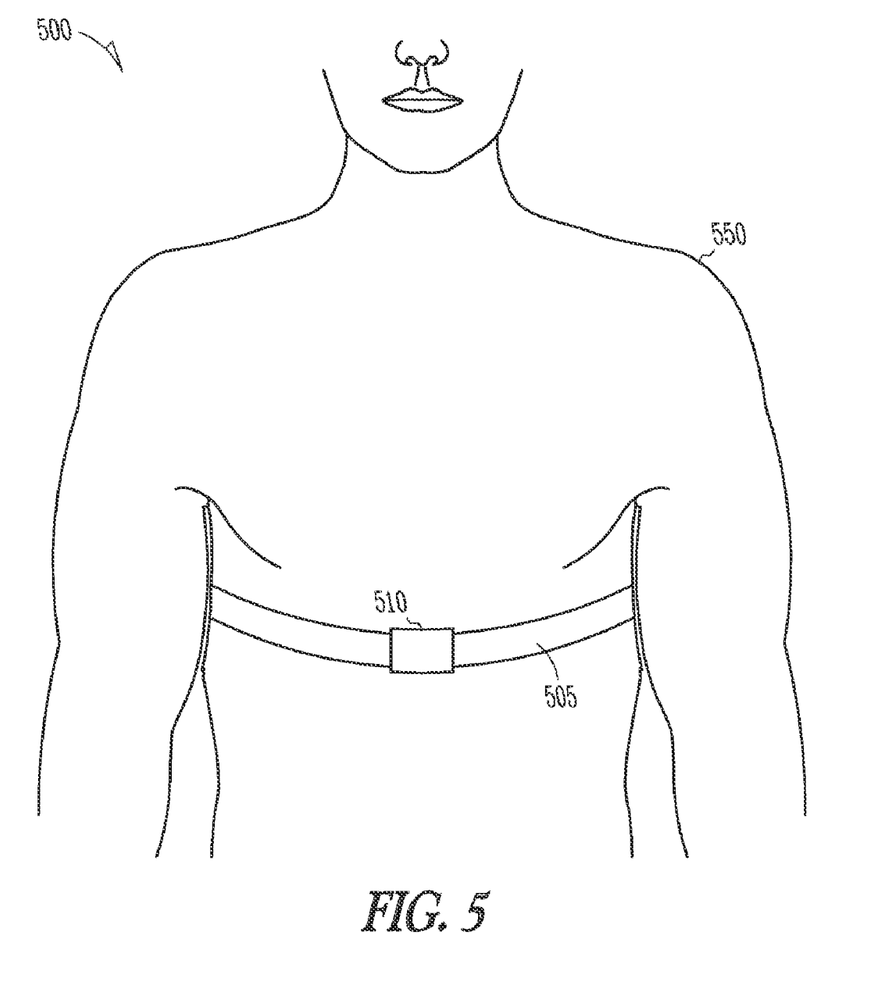
FIG. 5 is a schematic/block diagram illustrating position sensor components according to one example.

FIG. 5 is a schematic/block diagram illustrating generally, by way of example, but not by way of limitation, one example of implementing first apnea detector 105 by using a position sensor system 500 according to the present invention. System 500 includes a band 505 placed around the abdomen or thorax, and a sensor 510 to monitor position changes of the band.

In one example, the system 500 includes a band 505 located around the thorax to measure chest wall movement, and position sensor 510 that detects and records the movement. Band 505 may be any material capable of being located around the abdomen or thorax. Band 505 may be placed in any location capable of sensing movement correlated to respiration. Other position sensors may also be used for sensing respiration.

Figure 6:
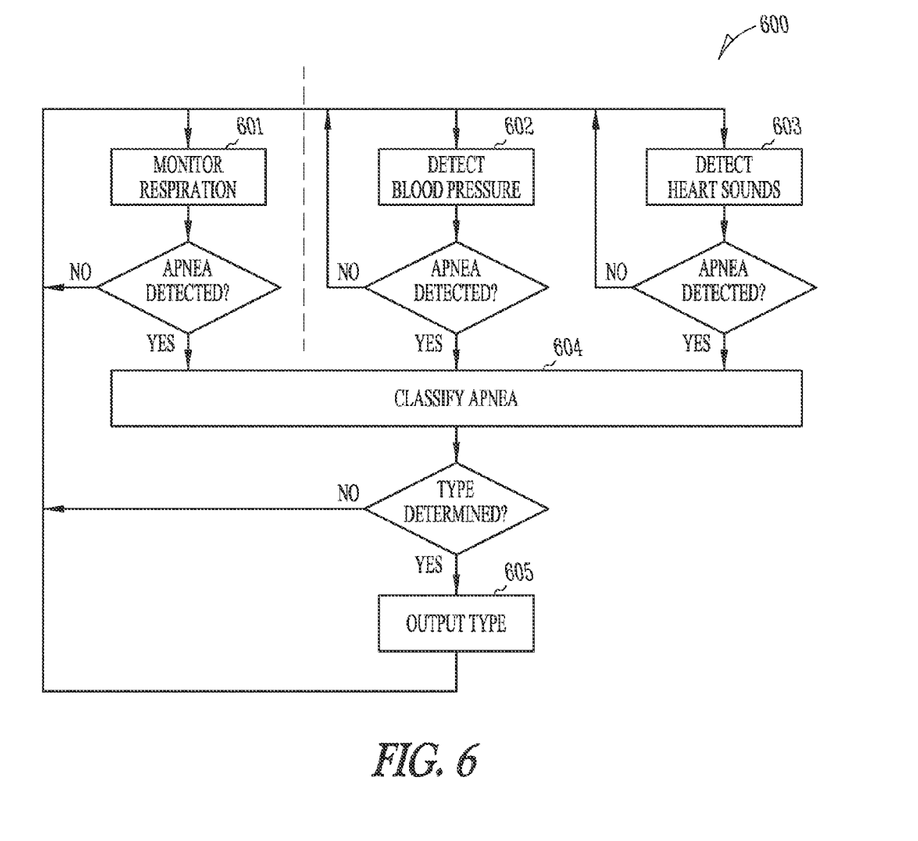
FIG. 6 is a flow chart according to one example.

FIG. 6 is a flow chart illustrating generally, by way of example, but not by way of limitation, one example of implementing an apnea classification method 600. At 601, first apnea detector 105 is monitoring the respiration of subject 150. In one example, the monitoring begins as system 100 is activated. In another example, the monitoring begins in response to a user command. In another example, the monitoring begins at a predetermined time or upon a predetermined triggering event. In one example, the monitoring lasts for a predetermined duration after it begins. In another example, the monitoring lasts for as long as system 100 is active. In another example, the monitoring begins on a recurring basis and may last for a specified duration.

At 602, second apnea detector 110 is detecting the blood pressure of subject 150. In one example, the detection begins as system 100 is activated. In another example, the detection begins in response to a user command. In another embodiment, the detection begins at a predetermined time or upon a predetermined triggering event. In one example, the detection lasts for a predetermined duration after it begins. In another example, the detection lasts for as long as system 100 is active. In another example, the detection begins on a recurring basis and may last for a specified duration.

At 603, second apnea detector 110 is detecting heart sounds of subject 150. In one example, the detection begins as system 100 is activated. In another example, the detection begins in response to a user command. In another embodiment, the detection begins at a predetermined time or upon a predetermined triggering event. In one example, the detection lasts for a predetermined duration after it begins. In another example, the detection lasts for as long as system 100 is active. In another example, the detection begins on a recurring basis and may last for a specified duration.

At 604, apnea classifier module 115 classifies apnea from information received from first apnea detector 105 and second apnea detector 110. At 605, apnea classification system output 120 displays the type of apnea determined at apnea classifier module 115.

In one example, at 604, apnea classifier module 115 receives data from first apnea detector 105 when an apnea event is detected. In another example, apnea classifier module 115 receives data from first apnea detector 105 when an apnea event is not detected. In one example, first apnea detector 105 continues monitoring subject 150 following the detection of an apnea event. In another example, first apnea detector 105 ceases monitoring subject 150 following the detection of an apnea event.

In another example, at 604, apnea classifier module 115 receives data from second apnea detector 110 when an apnea event is detected. In another example, apnea classifier module 115 receives data from second apnea detector 110 when an apnea event is not detected. In one example, second apnea detector 110 continues monitoring subject 150 following the detection of an apnea event. In another example, second apnea detector 110 ceases monitoring subject 150 following the detection of an apnea event.

At 604, apnea is classified from information received from monitoring respiration, 601, and at least one of detecting blood pressure, 602, and detecting heart sounds, 603. In one example, if the apnea type is distinguished, the result is stored within the apnea classifier module 115 or apnea classification system output 120 for later utilization. In another example, if the apnea type is distinguished, the result is used to begin therapy specific to the type of apnea present. In another example, if the apnea type is distinguished, the result is communicated to a third person, such as a doctor. In another example, if the apnea type is distinguished, the result is sent external to the apnea classification system 100. In another example, if the apnea type is distinguished, the result is utilized in a manner comprising at least one of being stored within the apnea classifier module 115 or apnea classification system output 120 for later utilization, being used to begin therapy specific to the type of apnea present, being communicated to a third person, being sent external to the apnea classification system 100.

In one example, at 604, if information is received that apnea is detected from monitoring respiration, 601, and information is received that apnea is detected from at least one of detecting blood pressure, 602, and detecting heart sounds, 603, type obstructive sleep apnea has been determined. In another example, at 604, if information is received that apnea is detected from monitoring respiration, 601, and information is received that apnea is not detected from detecting blood pressure, 602, or detecting heart sounds, 603, type central sleep apnea has been determined. In another example, at 604, if information is received that apnea is not detected from monitoring respiration, 601, and information is received that apnea is detected from at least one of detecting blood pressure, 602, and detecting heart sounds, 603, type obstructive sleep apnea has been determined. In another example, at 604, if information received from monitoring respiration, 601, detecting blood pressure, 602, and detecting heart sounds, 603, is conflicting, no apnea type has been determined, and system 100 continues to monitor for an apnea event.

In one example, at 604, apnea is classified according to Table 1.

TABLE 1

|  | Monitor Respiration | Detect Blood Pressure/Heart Sounds | Apnea Type Determined |
|---|---|---|---|
| Apnea Detected? | Yes | Yes | Obstructed Sleep Apnea |
| Apnea Detected? | Yes | No | Central Sleep Apnea |
| Apnea Detected? | No | Yes | Obstructed Sleep Apnea |
| Apnea Detected? | No | No | None |

In one example, at 604, if the apnea type is not distinguished, the information is discarded and apnea classifier module 115 continues to monitor information from first apnea detector 105 and second apnea detector 110. In another example, at 604, if the apnea type is not distinguished, the data is stored and apnea classifier module 115 continues to monitor information from first apnea detector 105 and second apnea detector 110. In another example, at 604, if the apnea type is not distinguished, the data is sent external to the apnea classification system 100.

It is to be understood that the above description is intended to be illustrative, and not restrictive. For example, the above-described embodiments (and/or aspects thereof) may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract is provided to comply with 37 C.F.R. §1.72 (b), which requires that it allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment.

What is claimed is:

1. An apparatus comprising:
   a respiration-based first apnea detector, comprising a respiration sensor providing cyclic information indicative of inhaling and exhaling;
   a non-respiration-based second apnea detector, comprising at least one of a blood pressure sensor and a heart sound sensor, the second apnea detector using information other than cyclic information indicative of inhaling and exhaling; and
   an apnea classifier module, coupled to the first and second apnea detectors, to distinguish between obstructive sleep apnea (OSA) and central sleep apnea (CSA) using information from both the first and second apnea detectors.

2. The apparatus of claim 1, in which the respiration sensor includes an impedance sensor.

3. The apparatus of claim 1, in which the respiration sensor includes a blood pressure sensor configured to extract respiration information from blood pressure information.

4. The apparatus of claim 1, in which the respiration sensor includes an accelerometer configured to extract respiration information from an acceleration.

5. The apparatus of claim 1, in which the respiration sensor includes a heart sound sensor configured to extract respiration information from heart sounds.

6. The apparatus of claim 1, in which the respiration sensor includes an acoustic sensor configured to extract respiration information from respiratory sounds.

7. The apparatus of claim 1, in which the respiration sensor includes a position sensor configured to extract respiration information from body movement.

8. The apparatus of claim 1, in which the respiration sensor includes a thermister configured to extract respiration information from a temperature variation.

9. The apparatus of claim 1, in which the non-respiration-based second apnea detector includes the blood pressure sensor, and wherein the blood pressure sensor is configured to be located in a pulmonary artery to measure a pulmonary artery pressure; and
   in which the apnea classifier module is configured to distinguish between obstructive sleep apnea (OSA) and central sleep apnea (CSA) using respiration information from the first respiration-based first apnea detector and pulmonary artery pressure information from the non-respiration-based second apnea detector.

10. The apparatus of claim 1, in which the non-respiration-based second apnea detector includes the blood pressure sensor, and wherein the blood pressure sensor is configured to be located in association with a ventricle to measure a ventricular pressure; and
    in which the apnea classifier module is configured to distinguish between obstructive sleep apnea (OSA) and central sleep apnea (CSA) using respiration information from the first respiration-based first apnea detector and ventricular pressure information from the non-respiration-based second apnea detector.

11. The apparatus of claim 10, in which the blood pressure sensor is configured to sense a left ventricle end diastolic pressure (LVEDP); and
    in which the apnea classifier module is configured to distinguish between obstructive sleep apnea (OSA) and central sleep apnea (CSA) using an increase in magnitude of a sensed LVEDP during a detected apnea.

12. The apparatus of claim 1, in which the non-respiration-based second apnea detector includes the heart sound sensor, the heart sound sensor comprising at least one of an acoustic sensor, a pressure sensor, and an accelerometer; and
    in which the apnea classifier module is configured to distinguish between obstructive sleep apnea (OSA) and central sleep apnea (CSA) using respiration information from the first respiration-based first apnea detector and heart sound information from the non-respiration-based second apnea detector.

13. The apparatus of claim 12, in which the heart sound sensor is configured to sense a first heart sound (S1); and
    in which the apnea classifier module is configured to distinguish between obstructive sleep apnea (OSA) and central sleep apnea (CSA) using an increase in a sensed S1 amplitude during a detected apnea.

14. The apparatus of claim 1, in which the non-respiration-based second apnea detector includes the heart sound sensor, the heart sound sensor comprising a position sensor; and
    in which the apnea classifier module is configured to distinguish between obstructive sleep apnea (OSA) and central sleep apnea (CSA) using respiration information from the first respiration-based first apnea detector and position information from the non-respiration-based second apnea detector.

15. The apparatus of claim 1, in which the non-respiration-based second apnea detector includes the heart sound sensor, the heart sound sensor comprising an activity sensor; and
    in which the apnea classifier module is configured to distinguish between obstructive sleep apnea (OSA) and central sleep apnea (CSA) using respiration information from the first respiration-based first apnea detector and activity information from the non-respiration-based second apnea detector.

16. A method to detect and distinguish between obstructive sleep apnea (OSA) and central sleep apnea (CSA), the method comprising the acts of:
sensing a respiration signal that includes cyclic variations indicative of inhaling and exhaling;
detecting at least one of a blood pressure signal and a heart sound signal, the detecting including using a component of the at least one of the blood pressure and the heart sound signal, wherein the component includes information other than the cyclic variations indicative of inhaling and exhaling;
detecting an apnea event from at least one of the respiration signal, the blood pressure signal, and the heart sound signal; and
distinguishing between OSA and CSA using information from the respiration signal and information from at least one of the blood pressure signal and the heart sound signal.

17. The method of claim 16, in which the act of sensing a respiration signal includes using an implantable sensor.

18. The method of claim 16, in which the act of sensing a respiration signal includes sensing a thoracic impedance.

19. The method of claim 16, in which the act of sensing a respiration signal includes extracting respiration information from a blood pressure signal.

20. The method of claim 16, in which the act of sensing a respiration signal includes sensing an acceleration and extracting respiration information from the acceleration.

21. The method of claim 16, in which the act of sensing a respiration signal includes sensing heart sounds and extracting respiration information from the heart sounds.

22. The method of claim 16, in which the act of sensing a respiration signal includes an acoustic sensor and extracting respiration information from the acoustic sensor.

23. The method of claim 16, in which the act of sensing a respiration signal includes sensing a temperature and extracting respiration information from the temperature.

24. The method of claim 16, in which the distinguishing between OSA and CSA includes using information from the respiration signal and information from the blood pressure signal.

25. The method of claim 24, in which the using information from the blood pressure signal includes using information from a pulmonary artery blood pressure signal for distinguishing between OSA and CSA.

26. The method of claim 24, in which the using information from the blood pressure signal includes using information from a ventricular blood pressure signal for distinguishing between OSA and CSA.

27. The method of claim 16, in which the distinguishing between OSA and CSA includes using information from the respiration signal and the heart sounds signal.

28. The method of claim 16, in which the detecting the blood pressure signal includes detecting a left ventricle end diastolic pressure (LVEDP) signal; and
in which the distinguishing between obstructive sleep apnea (OSA) and central sleep apnea (CSA) includes using an increase in magnitude of a sensed LVEDP signal during a detected apnea.

29. The method of claim 16, in which the detecting the heart sound signal includes detecting a first heart sound (S1) signal; and
in which the distinguishing between obstructive sleep apnea (OSA) and central sleep apnea (CSA) includes using an increase in a sensed S1 signal amplitude during a detected apnea.

30. An apparatus to detect and distinguish between obstructive sleep apnea (OSA) and central sleep apnea (CSA), the apparatus comprising:
means for sensing a respiration signal using cyclic information indicative of inhaling and exhaling;
means for detecting at least one of a blood pressure signal and a heart sound signal using information other than cyclic information indicative of inhaling and exhaling;
means for detecting an apnea event from at least one of the respiration signal, the blood pressure signal, and the heart sound signal; and
means for distinguishing between OSA and CSA using information from the respiration signal and information from at least one of the blood pressure signal and the heart sound signal.

* * * * *